Figure 1:
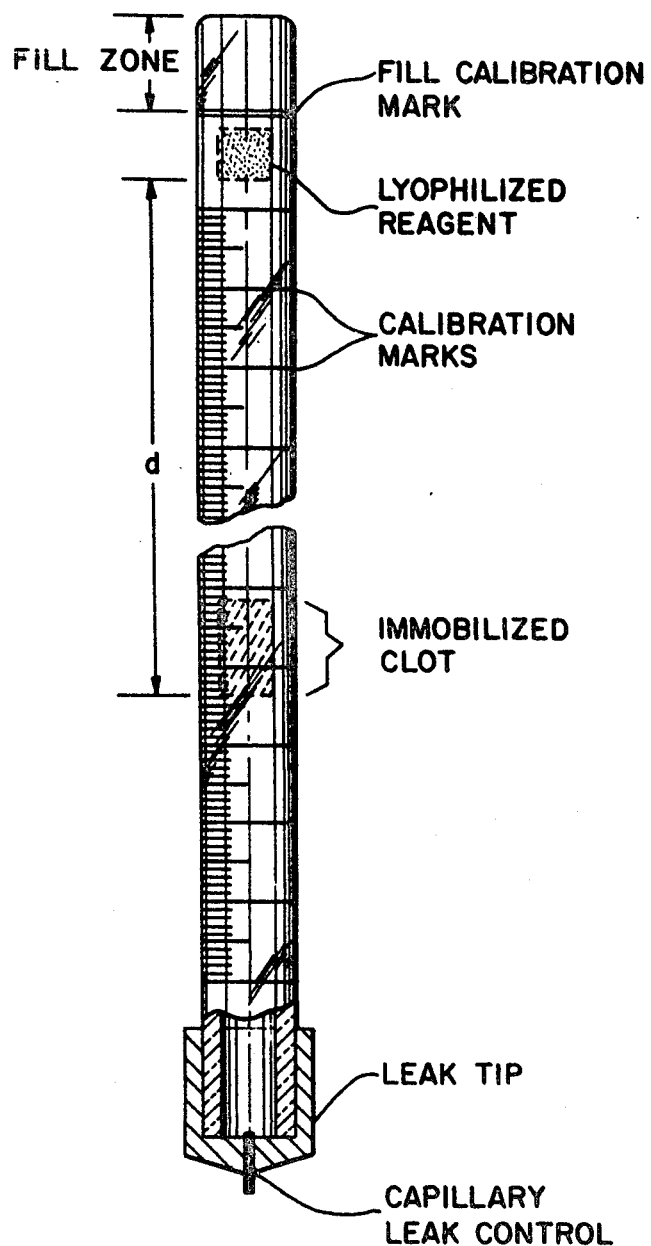

United States Patent [19]
Moyer et al.

[11] 3,951,606
[45] *Apr. 20, 1976

[54] APPARATUS FOR PROTHROMBIN TESTING

[75] Inventors: Rudolph H. Moyer, West Covina; Donald J. Sibbett, Cucamonga, both of Calif.

[73] Assignee: Geomet, Inc., Gaithersburg, Md.

[ * ] Notice: The portion of the term of this patent subsequent to Nov. 11, 1992, has been disclaimed.

[22] Filed: May 17, 1974

[21] Appl. No.: 470,893

[52] U.S. Cl. .................................. 23/253 R; 23/259
[51] Int. Cl.² .................. G01N 33/16; B01L 11/00
[58] Field of Search .............. 23/230 B, 253 R, 259, 23/292; 73/57, 64.1; 128/2 G, 2 M, DIG. 22

[56] References Cited
UNITED STATES PATENTS

| | | | |
|---|---|---|---|
| 2,171,823 | 9/1939 | Baker | 73/51 |
| 2,664,403 | 12/1953 | Weichselbaum | 23/292 X |
| 2,685,800 | 8/1954 | Natelson | 23/259 X |
| 3,233,975 | 2/1966 | McCormick | 23/259 |
| 3,434,859 | 3/1969 | Benjamin | 23/230 B X |
| 3,560,163 | 2/1971 | Mittleman | 23/253 R |
| 3,692,487 | 9/1972 | Sanz | 23/253 R |
| 3,838,013 | 9/1974 | Bergeron | 195/139 |

OTHER PUBLICATIONS
Chem. Abstr., V. 6: 1016 (1912).
J. Lab. & Clin. Med., V. 53, pp. 617–621 (1959).

*Primary Examiner*—Morris O. Wolk
*Assistant Examiner*—Timothy W. Hagan
*Attorney, Agent, or Firm*—David H. Semmes

[57] ABSTRACT

A manually operable, disposable diagnostic device which is useful for the rapid measurement of coagulation rates consists of a uniform bore reaction tube which may be used to take up the sample and contains the appropriate amounts of lyophilized reagents required to conduct individual tests such as that for prothrombin time. In an example, calibration marks on the tube have been correlated in terms of prothrombin times. The position at which a liquid sample becomes immobilized as it descends down the tube corresponds to the test time. The rate of descent is controlled by a limiting orifice or by inclining the tube to the vertical axis.

16 Claims, 3 Drawing Figures

APPARATUS FOR PROTHROMBIN TESTING

BACKGROUND OF THE INVENTION

The present invention relates to a device for rapid assessment of coagulation rates. In the preferred embodiment, the clotting ability of small samples of whole blood, or plasma is assessed on the basis of measuremets such as prothrombin time, partial thromboplastin time or similar tests.

The natural phenonmenon of blood coagulation is complex, involving a sequence of enzymatic and physical interactions to convert fluid blood into an adhesive mass. The major processes involve the conversion of the proenzyme, prothrombin, to the enzyme, thrombin and the action of thrombin upon fibrinogen to form fibrin. The fibrin separates as long fibers or threads, which are extremely adhesive. These threads stick to each other, blood cells, tissues, and foreign substances to form a three dimensional network or clot. The adhesiveness causes the clotted blood to hold together and stick firmly to injured tissues to prevent hemorrhage. The overall clotting sequence can be represented as:

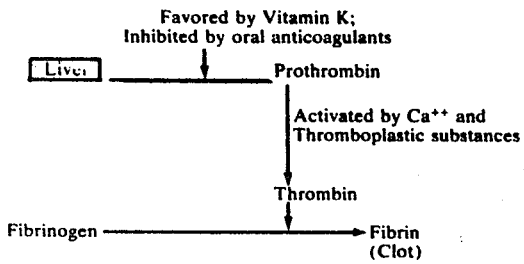

Blood does not normally clot in the vascular system, since thrombin is present in the inactive form, prothrombin, which becomes activated to thrombin when blood escapes due to injury or is withdrawn from the blood vessels. Prothrombin activation is accomplished by substances known as thromboplastins which occur in blood platelets and various tissues, particularly lung and brain. In some diseases, partial prothrombin activation can occur in the blood vessels and result in a thromboembolic condition. This condition is hazardous in diseases such as the following, for which treatment with various anticoagulants is frequently prescribed to prevent the formation of intravascular thrombi and maintain normal hemostatis:
1. myocardial infarction
2. rheumatic heart disease
3. cerebrovascular disease
4. venous thrombosis
5. pulmonary embolism The administration of anticoagulants as part of the treatment for these diseases is largely empirical and dosage is regulated on a daily basis until the response of an individual patient to the anticoagulant becomes established. Even after regulation of the dosage for long-term treatment, patient response is generally monitored on a bi-weekly or monthly schedule.

The oldest and most widely used method for monitoring patient response to anticoagulant therapy is the one-stage prothrombin time proposed by Quick, or some adaptation of this basic method. In the one-stage prothrombin time measurement, blood is collected in sodium citrate or oxalate, which chelate calcium and prevent prothrombin activation prior to the start of the measurement. The blood is centrifuged and an aliquot of plasma mixed with an excess of thromboplastic extract of brain or lung tissue which contains sufficient calcium to overcome the effect of the chelating agent. Mixing is carried out rapidly under controlled conditions and the time required for incipient clot formation defined as the prothrombin time. Clot formation may be observed visually or measured by means of commercially available mechanical devices. When the measurement is carried out at 37°C, normal human plasma usually has a prothrombin time of 12 seconds.

In current clinical practice, measurements of prothrombin time are made on blood samples drawn from patients and then transported to a laboratory for analysis. Though these measurements are relatively easy to perform and do not involve the use of complex or expensive reagents, they do require the time of specifically trained personnel, along with the use of unique equipment and laboratory facilities. The need for a laboratory analysis introduces a significant delay between the time a sample is drawn and that at which the analytical result is available to aid in the regulation of thereapy. While the delay is not usually of a critical nature, it represents an inconvenience to both the patient and prescribing physician. A major shortcoming of the current methodology is the need for repeated venipuntures over a long period of time to obtain the blood samples necessary for monitoring anticoagulant therapy for each patient after a regimen has been established. Since the patients concerned are frequently elderly, these venipunctures can be difficult to carry out and involve some trauma to the patient.

The present inventon describes a device which may be applied to rapid measurements of prothrombin time on a drop of uncoagulated whole blood obtained from a finger puncture. The device includes all of the reagents and apparatus necessary for carrying out a prothrombin time measurement. The device thus represents a significant improvement over the prior art. By means of the device, measurements of prothrombin time can be carried out in approximately 2 minutes to produce a definitive result, eliminating delays and the need for trained personnel with access to specific laboratory facilities. The sample required for each measurement is a drop of uncoagulated whole blood from a finger puncture, eliminating the inconvenience of venipuncture necessary in the methodology of the prior art. In addition, there is no critical time for reading the result. The test may be started and the result veiwed and recorded at the convenience of the user. The final position of the result endures nearly indefinitely.

Prothrombin times are usually measured in small containers such as test tubes or cells into which a plasma sample is placed together with reagents such as one of various commercial thromboplastin reagents together with extra calcium, if required. The time from mixing of the reagents and the sample to clot formation may be measured by various procedures including simple observation by eye, by optical instrumentation which detects changes in transmission of the sample, by fibrometers which detect the adhesion of the clots to wires or fibers, by measurement of conductivity changes and by various measurements of viscosity increases. The initial one stage prothrombin time was developed, demonstrated and popularized by Quick. This test is sensitive to blood Factors V (the Labile Factor or Proaccelerin), VII (Proconvertin) and X (Stuart-Power Factor) as well as Prothrombin (Factor II). In determination of the prothrombin time by the Quick method the factors with the exception of prothrombin are assumed present in excess. However, Factors VII and X may decrease during anticoagulant therapy.

PRIOR ART

In the past, there have been various devices employed in order to measure coagulation rates; however none possesses the ease and rapidity of the present invention.

For example, U.S. Pat. No. 2,171,823 (Baker) utilizes a capillary viscometer to measure the quantity of sugar required to make various jellies from fruit juices. Although this device employs a capillary tube, the tube is taught to be flow regulating. By contrast, the capillary tube of the instant invention is taught to have a diameter sufficiently large as to eliminate effects of blood or sample viscosity. Baker shows a logarithmic dependence of flow vs. sugar content or relative viscosity vs. capillary length. This dependence is normal for viscosity measurements. The disclosed device shows a linear correlation between prothrombin time and distance travelled down the tube. The disclosed device is a method of measuring the reaction time of specific chemical components of blood. For this measurement to be meaningful it must be conducted under conditions where blood viscosity effects are minimized.

U.S. Pat. No. 3,486,859 (Greiner et al) teaches a device for measuring the coagulation time of blood samples. The Greiner invention is essentially a method of mixing blood with added reagents and pumping these components back and forth through a capillary by use of air pressure. The time at which the flow through the capillary is restricted so that further pumping cycles cannot take place without an increase in pressure is measured as the coagulation time. This complex device uses a relatively large amount of blood (usually 20 ml) and is dependent on detection of the amplitude of pressure changes during each pumping stroke for determination of the coagulaton time. It utilizes a capillary connection between the reagents and blood sample to amplify the effects of coagulation. The disclosed device uses a reaction tube through which samples and reagents pass under the influence of gravity. The distance down which the blood or plasma sample passes after admixture with reagents is the reaction time measure. No pumping equipment or pressure sensors are utilized.

Prothrombin time measurements is the subject of U.S. Pat. No. 3,560,162 (Mittleman). This device pushes blood (or plasma) and reagents between two compartments formed by a piston containing axial apertures of various designs. This device bears no resemblance physically or in the principles employed to the disclosed device.

U.S. Pat. No. 3,550,581 (Boyle) describes an invasive device for measuring the tendency of the blood to thrombose. After insertion of a hypodermic needle into a vein the device measures the flow of blood into a flexible plastic tube until clotting occurs. The volume collected is measured against time until the termination of thrombosis. This time and volume is considered a measure of the tendency of a patient to thrombose. The diameter of the smooth measuring tube was specified at 0.020 to 0.040 inches. This measurement is made without the additon of chemical reagents as in this disclosure and measures the clotting time of whole blood not the reaction limited by prothrombin and related blood factors.

U.S. Pat. No. 3,525,254 (Milanes) is a method of separating blood clots from serum in order to determine the rate of clot retraction and fibrinolysin activity. It consists of an invertable tube with various means of containing clots in contact with the tube closure. The patent has no direct relationship with the disclosed device.

U.S. Pat. No. 3,434,859 (H. Benjamin) has described an electrostatic method for internally coating a capillary tube with powdered material by inducing an electrostatic charge on the inner surface. Such coated capillaries are particularly suitable for use in the measurement of the sedimentation rates of blood when the powder coating is dipotassium sequestrine. This technique is not utilized in placement of the chemical reagents used in the disclosed procedure. This disclosure requires that the regents be placed in a finite limited position so that appropriate reaction concentrations may be rapidly achieved. The reaction time or equivalently, distance down the tube is measureable from the tube circumference at which all the thromboplastin reagent has been dissolved in the sample. Thus a continuous coating of the tube by reagent as demonstrated by Benjamin is not useful in the reaction tube of the disclosure.

Russian Patent 52422R-A (251,909) (V. A. Bandarin, E. P. Ivanov and V. A. Syatkovskii) utilizes a tube with a calibrated capillary end for measuring the amount of serum separated upon coagulation of a blood sample. This device is for a volumetric measuring procedure after separation of clots from whole blood.

SUMMARY DESCRIPTION OF THE INVENTION

The disclosed invention consists of a reaction tube containing specially prepared and positioned reagents which are appropriate for reaction with blood, plasma or other fluids. To the top of the tube a small sample of the liquid to be tested is added. It descends, dissolving the reagents, and comes to rest at a position correlatable with its reaction duration. The measure of the velocity of the reaction is the position down the length of the tube at which the slug sample of liquid becomes immobile. With use of the appropriate reagents, this position is directly correlatable with the prothrombin time of a blood or plasma sample.

In order to operate effectively and reproducibly, the interior surface of the tube must be uniformly wettable by the sample. Prior to use the tube has positioned within it at a specified position, the chemical reagent consisting of thromboplastin reagents and some additives in the appropriate quantities to bring about the Prothrombin Reaction when dissolved in the liquid sample. These reagents are lyophilized at a position within the tube immediately below a calibration mark indicating the volume of sample with which the tube is to be filled. After lyophilization, the tube is sealed in a moisture-proof pouch from which it is removed only at time of use.

Alternatively, the reagent can be pre-mixed with the sample before entry into the reaction tube or cylinder. This later technique is, however, usually less convenient in that the time period between the pre-mixing and viscosity measurement stages can become important.

The tube, which is of a substantially uniform bore, is used by placing the sample of blood or plasma in its upper end. For a tube of appropriate diameter, the sample may be introduced by touching the filling end to the surface of the sample. By capillary action the sample is drawn up. It is allowed to rise in the inverted tube until the meniscus reaches a calibrated fill mark. At this moment, the tube is turned upright with the sample at the top end. Under the influence of gravity, this measured volume of sample or liquid slug travels downward through the lyophilized reagents which are required for reaction. After dissolution of the reagents the liquid plug continues to descend the tube until coagulation occurs. The distance of travel from the position of the bottom of the lyophilized reagents to the bottom of the coagulum may be used as a direct measure of the reaction rate. For several tube preparations this distance has been conveniently calibrated against Prothrombin Time as determined by the standard one-stage Quick test. See: A. J. Quick: Amer. J. Med. Sc. 190, 501 (1935); Proc. Sc. Exper. Biol. and Med., 42 788 (1939); Amer. J. Clin. Path., 15, 560 (1945); Thromb. Diath. Haemorrh., 2, 226 (1958); Amer. J. Med. Sci., 246 2517 (1963). The plot of Prothrombin Time vs. distance travelled down the tube is a simple linear function.

In principle, the tube might be made as long as necessary to utilize unrestricted flow rates of the liquid plug down the tube; for convenience, several methods of restricting the rate of descent have been employed. For example, orifices have been placed on the lower end of the tube which restrain the air leak rate from the tube volume contained below the liquid sample slug. The tube may also be placed at an angle to the vertical whence the sample weight acts as the driving force for descent of the liquid plug and is multiplied by a factor equal to the cosine of the angle which the tube makes with the vertical axis. Similarly, the rate of descent can be controlled by an internal wall covering or by physical projections within the internal surface of the cylinder. In either event the final stopping position is a direct measure of the Prothrombin Time of the sample.

In normal clinical practice, Prothrombin Times as obtained by the procedure of Quick are determined at 37°C. It has been determined that prothrombin distances as determined by the reaction tube method may be conveniently obtained at room temperatures provided a calibration plot is constructed which relates the two sets of data (i.e., the standard Prothrombin Times at 37°C with the Reaction Tube Prothrombin Times at ambient temperatures such as 22°–23°C).

For reproducible performance of the disclosed Prothrombin reaction tubes, the physical and chemical parameters which control the reaction rate and rate of liquid movement within the tubes must be carefully specified. These parameters include: (a) internal tube diameter and its variation, (b) cleanliness and uniformity of the inner tube surface, (c) sample volume, (d) reagent composition and position, (e) rate of reagent solubility and/or reagent density and porosity in the tube, (f) absolute quantity of reagents, (g) reaction temperature, (h) rate of leakage of air from the volume under the sample slug or the angle to the vertical at which the tube is positioned. A relatively narrow set of specifications on each of these parameters is required. The most significant parameter is choosing the internal diameter of a reaction tube which will be large enough to allow the uncoagulated liquid sample to flow downwardly, under the influence of gravity, after the initial combination of liquid sample and reagents. This diameter is chosen also so that when the liquid sample has coagulated and become immobilized therein a convenient length of the tube has been traversed. As illustrated hereinafter, for a preferred embodiment, a 1.8 mm diameter is advantageously employed with whole blood or plasma.

The primary object of the present invention is to provide a device for measuring a change in viscosity of a sample over a period of time.

A further object of the present invention is to provide a manually operable diagnostic device which is useful for the rapid measurement of coagulation rates.

Still other objects, features and attendant advantages of the present invention, together with various modifications, will become apparent to those skilled in the art from a reading of the following detailed description of the preferred embodiment constructed in accordance therewith, taken in conjunction with the accompanying drawings.

EMBODIMENT OF THE INVENTION

One example of an embodiment of the disclosed device is shown in FIG. 1. It may be varied in several forms such as the one diagrammed in FIG. 2.

Figure 3:
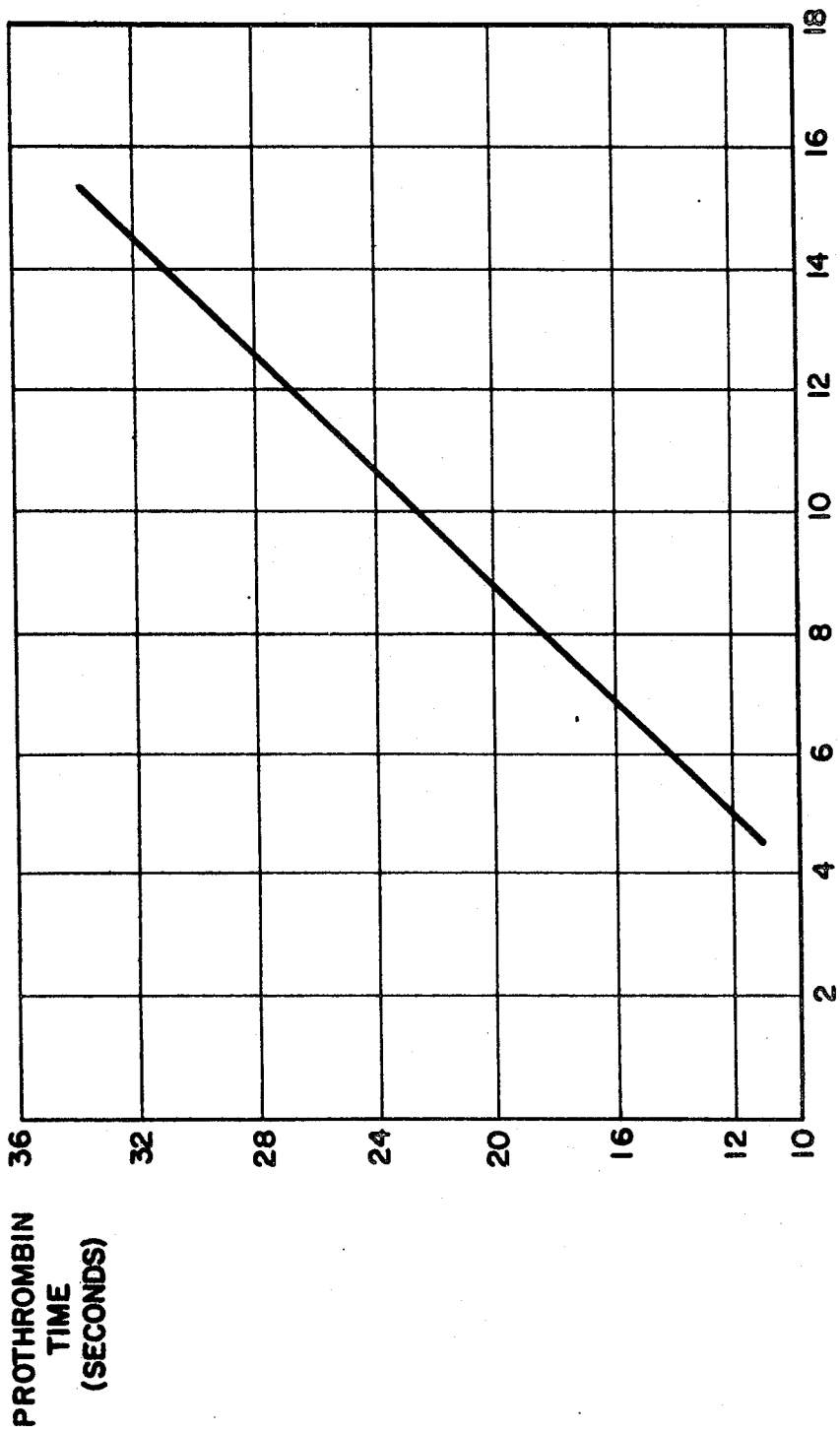

FIG. 1 shows schematically a small uniform bore glass tube with a 1.8 mm (±2%) diameter opening, 18 cm in length, which is calibrated to be filled with 35 microliters of blood or plasma at the indicated fill line. The tube length is calibrated in mm markings extending downward from the bottom edge of the deposit of lyophilized reagent. The distance, $d$ is the measure of the travel of the reacting liquid sample slug to the point of immobilization which is caused when clotting takes place. FIG. 3 shows calibration data for such a reaction tube when a 20 mm length of 0.006 inch i.d. stainless steel capillary was used as the air leak control.

Under the conditions of the experiment at 23°C each cm of travel of the clot down the tube was equivalent to 2.1 seconds of Prothrombin time as measured at 37°C. In these experiments the co-efficient of variation was ± 6–8%.

A number of calibrations of this type have been obtained at varying temperatures, tube diameters and lengths, air leak rates and sample volumes. The absolute numerical values obtained have retained the linear correspondence between the prothrombin times as measured by the standard clinical laboratory method and the reaction tube of this disclosure. Thus, a very convenient and simple method for measuring the one-step prothrombin time and partial prothrombin times has been demonstrated.

One of the major factors relating to performance of the prothrombin reaction tube has been optimization of the thromboplastin reagent in terms of reactivity, mechanical stability and rate of solution. A number of commerical thromboplastin preparations have been tested. All show adequate reactivity characteristics when absolute quantities were used such that when reconstituted from a dry state in the sample volume (i.e. 35 Microliters in the illustration above) the concentrations prescribed are achieved. This approximates 10 mg/ml for a number of commercial preparations. However, in order to make the freeze-dried preparation mechanically stable in the tube, gelatin was added at a concentration of 10 mg/ml. Porosity was achieved so that rapid dissolution of the reagents in the sample occurred by addition of a finely divided extender. The extender employed in the preparation used in acquiring the data displayed in FIG. 3 was Cab-O-Sil, fumed silica grade M-5, at a concentration of 5 mg/ml.

The thromboplastin reagent was made up in solution at the concentrations indicated. A 30 microliter portion was positioned by use of an automatic micropipette within a clean, frozen (−20°C) reactor tube at a position centered at 2.2 cm from the upper end. Tubes were transported to a lyophilizer, freeze-dried, placed in dry containers at 5% RH and stoppered. By this procedure a porous reagent plug was formed having a dimension of approximately 1 cm in height within each tube. Tubes were stored at ambient temperature until needed. An indefinitely long shelf life resulted.

Figure 2:
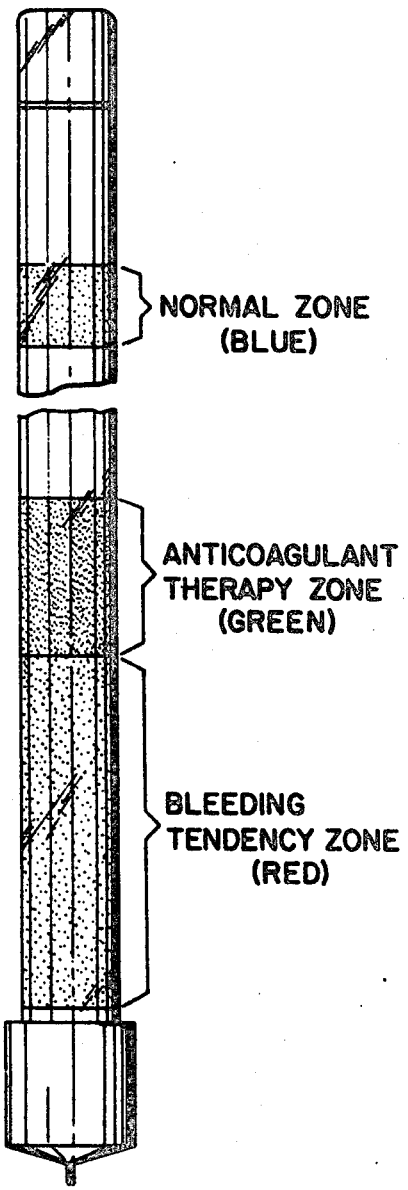

Tubes prepared in this fashion may be calibrated in terms of zones expressing the significance of the results obtained FIG. 2 shows an example of a tube which might be used to routinely check the effect of anticoagulant therapy. A small normal zone corresponding to prothrombin times of 12–14 seconds has been represented by a blue band. A zone indicating the desired response to anticoagulant dosage has been indicated by a green zone. This range corresponds to 18 to 22% prothrombin acitivity. The lowest range corresponds to further suppression of the prothrombin activity function.

The technique described above may be adapted to measurement of other blood and plasma clotting properties such as the total prothrombin time, prothrombin consumption time, the two-stage prothrombin assay, and assays of factors V, VIII, and IX.

In addition, the reaction tube may be used with reactions involving microquantities of sensitive reagents where a fixed reaction time is desired before the products from blood, plasma or serum reactions are examined spectrophotometrically or colorimetrically.

Furthermore, appropriate variations in the composition of the reagents according to conventional methods for carrying out the respective analyses permits the device to be used for such measurements as, polymerization reactions, assay of proteolytic enzymes, urokinase activity, fibrinogen preparation, individual blood clotting factors, and any other measuremets which would be readily obvious to one skilled in the art when confronted with this disclosure.

The precise tube dimensions specified in the example above should not be considered as limiting. The reaction tube dimensions may be varied so as to achieve any desired discrimination and precision in the resultant data. Tube dimensions in conjunction with the flow rate utilized may be varied conveniently for any application.

We claim:

1. Apparatus for reproducibly measuring changes of viscosity in a liquid sample subject to an increase in viscosity after combination with at least one reagent capable of altering said sample viscosity comprising in combination:
   A. a uniform bore reaction tube having an internal diameter sufficiently large so as to substantially eliminate effects of initial sample viscosity, wherein said combination further comprises;
   B. means at a first end of said uniform bore reaction tube for receiving said sample and combining said sample with said at least one reagent, and
   C. means to reproducibly gauge the approximate position from said first end at which said liquid and reagent combination travels downwardly and becomes immoblized due to said increase in viscosity wherein said gauge means includes calibration means operable to visually gauge the time for said viscosity increase as a direct function of said downward travel wherein said calibrated gauge means includes a restriction proximate the second end of said uniform bore reaction tube comprising a limiting orifice.

2. Apparatus of claim 1 in which said calibrated gauge means includes graduated markings.

3. Apparatus of claim 1 in which said calibrated gauge means is also calibrated for inclinations of said reaction tube to various angles from the vertical.

4. Apparatus of claim 1 in which said calibrated gauge means includes designated zones.

5. Apparatus of claim 1 in which the interior surface of the reaction tube is uniformly wettable by a liquid sample.

6. Apparatus of claim 1 in which said means for receiving said sample includes a calibration mark indicating the volume of sample with which the first end of said tube is to be filled.

7. Apparatus of claim 1 in which said at least one chemical reagent comprises thromboplastin reagents and additives in quantities sufficient to cause a prothrombin reaction when dissolved in a liquid sample of whole blood or plasma.

8. Apparatus of claim 1 in which said first end of said reaction tube contains a chemical reagent at a specified position.

9. Apparatus of claim 8 in which the chemical reagent is lyophilized.

10. Apparatus of claim 8 in which the chemical reagent is immediately below a calibration mark indicating the first end of said volume of sample with which the tube is to be filled.

11. Apparatus of claim 10 in which the chemical reagent is lyophilized.

12. Apparatus of claim 8 in which the chemical reagent is in the form of a reagent plug.

13. Apparatus of claim 12 in which said reagent plug is approximately 1 cm. in height within the reaction tube.

14. A manually operable diagnostic device for the determination of coagulation rates of a fluid sample after combination with a lyophilized reagent comprising in combination:
   A. a reaction tube having an internal diameter sufficiently large so as to substantially eliminate initial viscosity effects of a liquid sample,
   B. said tube having a first open end and including at least one lyophilized reagent in the form of a reagent plug positioned within said tube proximate said first end,
   C. said tube further including calibration means below said first end, said calibration means operable to visually gauge the time to coagulation of a liquid sample after contact with said lyophilized reagent as a direct function of the distance a liquid sample introduced into said first end descends below said positioned lyophilized reagent to a position of immobilization.

15. A manually operable diagnostic device as in claim 14 in which said at least one lyophilized reagent comprises thromboplastin and calcium and the fluid sample is selectable from a group comprising whole blood and plasma.

16. A manually operable diagnostic device as in claim 14 wherein said calibration means further comprises a limiting orifice proximate the second end of said tube.

* * * * *